United States Patent [19]

Mest et al.

[11] Patent Number: 5,843,938
[45] Date of Patent: Dec. 1, 1998

[54] TREATMENT OF ATHEROSCLEROSIS

[75] Inventors: Hans-Juergen Mest, Quickborn; Wolfgang Stenzel, Reinbek, both of Germany

[73] Assignee: Beiersdorf-Lilly GmbH, Hamburg, Germany

[21] Appl. No.: 725,601

[22] Filed: Oct. 3, 1996

Related U.S. Application Data

[60] Provisional application Nos. 60/008,339 Dec. 7, 1995 and 60/025,738 Sep. 10, 1996.

[30] Foreign Application Priority Data

Oct. 3, 1995 [EP] European Pat. Off. .............. 95306999

[51] Int. Cl.$^6$ ................................................. A61K 31/44
[52] U.S. Cl. .............................................. 514/210
[58] Field of Search .............................................. 514/210

[56] References Cited

U.S. PATENT DOCUMENTS

| | | | |
|---|---|---|---|
| 4,935,414 | 6/1990 | Stenzel et al. | 514/210 |
| 5,145,849 | 9/1992 | Stenzel et al. | 514/210 |

FOREIGN PATENT DOCUMENTS

| | | |
|---|---|---|
| 297380 | 1/1989 | European Pat. Off. . |
| 95/08532 | 3/1995 | WIPO . |

OTHER PUBLICATIONS

D. Baumgart et al., "Characterization of the inotropic ad arrhythmogenic action of the sodium channel activator BDF 9148: a comparison to its S–enantiomer BDF 9196, to its congener DPI 201–106, to norepinephrine, and to ouabain," Basic Research in Cardiology, 89 (1), 61–79 (1994).

Dr. Siegfried Klumpp et al., Neues aus Pharmakologie und Toxikologie, Krankenhauspharmazie, 11 (7), 298–299 (1990).

CA: 115:183093 Stenzel et al., 1991.

*Primary Examiner*—Theodore J. Criares
*Attorney, Agent, or Firm*—Roger S. Benjamin; James P. Leeds; David E. Boone

[57] ABSTRACT

The use of a compound of the formula:

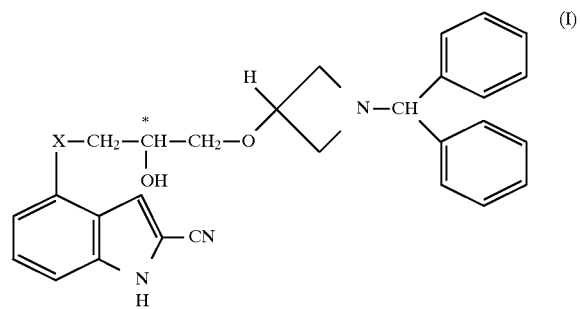

in which X is —O— or —NH—, or a pharmaceutically-acceptable acid addition salt thereof, in the treatment of atherosclerosis.

5 Claims, No Drawings

TREATMENT OF ATHEROSCLEROSIS

This application claims the benefit of US Provisional application Ser. No. 60/008,339 (Attorney Docket No. P-1031), filed Dec. 7, 1995, and U.S. Provisional application Ser. No. 60/025,738, filed Sep. 10, 1996.

BACKGROUND OF THE INVENTION

This invention relates to the use of organic compounds in the treatment of atherosclerosis.

Certain indolyl compounds are disclosed in U.S. Pat. Nos. 4,935,414 and 5,145,849, and in European Patents 0 297 380 and 0 439,796, for their inotropic and anti-arrhythmic action.

Atherosclerosis is a major risk factor and an important cause of death especially from cardiovascular diseases in industrial countries. The pathogenesis of atherosclerosis is unsolved in many points. It is accepted that atherosclerosis begins with local injury to the arterial endothelium which results in proliferation of arterial smooth muscle cells with deposition of lipid and accumulation of macrophages. As the atherosclerotic plaque develops it progressively obstructs more and more of the arterial vessels and can thus lead to ischemia or infarction in different tissues or organs.

It has now been found that certain indolyl compounds of the above-mentioned kind have useful anti-atherosclerotic properties. Chemical microanalysis of conventional human coronary artery plaques revealed a decrease in progressive mural calcium overload and the severity of plaque formation, with the use of the compound.

SUMMARY OF THE INVENTION

The present invention provides a method for treating a human suffering from or susceptible to atherosclerosis, which comprises administering an effective anti-atherosclerotic amount of a compound of the formula:

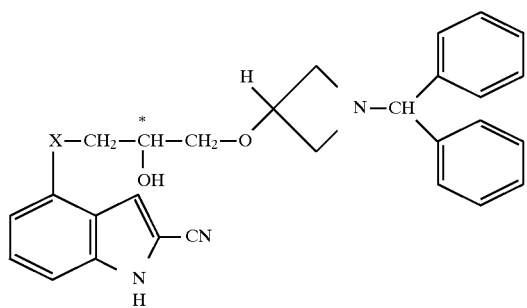

wherein X is —O— or —NH—, or a pharmaceutically-acceptable acid addition salt thereof.

The present invention also provides the use of a compound of the formula:

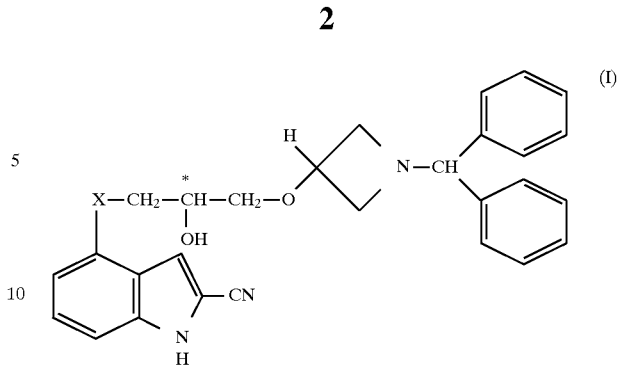

wherein X is —O— or —NH—, or a pharmaceutically-acceptable acid addition salt thereof, in the treatment of atherosclerosis. More particularly, the invention comprises the use of the above compounds, or a pharmaceutically-acceptable acid addition salt thereof, in the preparation of a drug for treating atherosclerosis.

DETAILED DESCRIPTION OF THE INVENTION

The formula (I) compounds are otherwise referred to as 4-[3-(1-diphenylmethylazetidin-3-oxy)-2-hydroxypropoxy]-1H-indole-2-carbonitrile and 4-[3-(1-diphenylmethylazetidin-3-oxy)-2-hydroxypropylamino]-1H-indole-2-carbonitrile. They have an asymmetric center indicated by the asterisk in the above formula (I), and this means that enantiomers of the compound exist. It should be understood that the racemate (S,R), the S-enantiomer, or the R-enantiomer, or mixtures thereof, can be employed in the present invention. It is preferred to utilize the S-enantiomer when X is —O— and the R-enantiomer when X is —HN—.

A preferred compound of formula (I) for use in the present invention is the compound in which X is —O—.

It has been found that the compound of formula (I) significantly decreased the total cholesterol content of cells cultured from atherosclerotic lesions (fatty streaks, plaques) of human aorta. The cholesterol accumulation caused by atherogenic serum from coronary atherosclerotic patient was decreased in cells cultured from normal human aortic intima.

The compounds of formula (I) can also be utilized in pharmaceutically-acceptable acid addition salt form. Suitable acid addition salts are the pharmaceutically-acceptable, non-toxic addition salts with suitable acids, for example hydrochloric or phosphoric acids, or with organic acids, such as organic carboxymaleic, malic, citric, tartaric, fumaric, salicylic, or organic sulphonic, 2-hydroxyethane sulphonic, p-toluenesulphonic, or naphthalene-2-sulphonic acid.

The identification of those patients who are in need of treatment for atherosclerosis is well within the ability and knowledge of one skilled in the art. For example, individuals who are either suffering from clinically significant atherosclerosis or who are at risk of developing clinically significant atherosclerosis are patients in need of treatment for atherosclerosis. A clinician skilled in the art can readily determine, by the use of clinical tests, physical examination and medical/family history, if an individual is a patient in need of treatment for atherosclerosis.

An effective anti-atherosclerotic amount of a compound of above-mentioned formula is an amount which is effective in inhibiting development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of the atherosclerosis. It is further understood and appreciated by those skilled in the art that successful treatment for atherosclerosis can include prophylaxis in preventing atherosclerotic lesion or plaque formation, and thus controlling or preventing atherogenesis.

For the purpose of the invention, the compounds of formula (I) may be administered by various routes, for example by the oral or rectal route, topically or parenterally, for example by injection or infusion, being usually employed in the form of a pharmaceutical composition. Such compositions are prepared in a manner well known in the pharmaceutical art. In making the composition the active ingredient will usually be mixed with a carrier, and/or enclosed within a carrier which may, for example, be in the form of capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatine capsules, suppositories, injection solutions, suspensions, sterile packaged powders and as topical patch. The preferred formulations are for oral dosage and are especially in tablet or capsule form.

Some examples of suitable carriers are lactose, dextrose, sucrose, sorbitol, mannitol, starches, ethylcellulose, gum acacia, calcium phosphate, alginates, tragcanth, gelatine, syrup, methyl cellulose, methyl- and propyl-hydroxybenzoate, talc, magnesium stearate and mineral oil. The composition of the injection may, as is well known in the art, be formulated so as to provide quick, sustained or delayed release of the active ingredient after administration to the patient.

Where the composition is formulated in unit dosage form, it is preferred that each unit dosage form contains from 1.0 mg to 30.0 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compound is effective over a dose range from 0.5 mg to 30 mg, more usually seems to be the dose range from 3 mg to 10 mg. Usually twice a day. However, it will be understood that the amount administered will be determined by the physician in the light of the relevant circumstances, including the condition to be treated and the chosen route of administration; therefore, the above dosage ranges are not intended to limit the scope of the invention in any way.

The following Example demonstrates the activity of a compound of formula (I) in human cell culture method.

EXAMPLE

The anti-atherosclerotic and anti-atherogenic effects of S-4-[3-(1-diphenylmethylazetidin-3-oxy)-2-hydroxypropoxy]-1H-indole-2-carbonitrile were demonstrated in the following manner.

Materials and Methods

Cell Culture

Subendothelial cells were isolated from grossly normal intima or atherosclerotic fatty streaks and plaque by dispersion of human aortic tissue with 0.15% collagenase (Orekhov, A. N. et al., *Exp. Mol. Pathol.* 1985, 42:117–137; Orekhov, A. N. et al., *Exp. Mol. Pathol.* 1985, 43:187–195). The autopsy material was taken from men aged 40 to 65 years who had died suddenly from myocardial infarction within 1–3 hours after death. Enzyme-isolated cells were suspended in Media 199 (Gibco BRL, Grand Island, N.Y.) containing standard additives: 2 mM L-glutamine, 100 U/ml penicillin, 100 µg/ml streptomycin, 2.5 µg/ml Fungizone and 10% of fetal calf serum (FCS). Cells were seeded into 96-well tissue culture plates at a density of $2.8 \times 10^4$ cells per well. The cells were cultured at 37° C. in a humidified $CO_2$-incubator (95% air and 5% $CO_2$) (Orekhov, A. N. et al. *Atherosclerosis* 1986, 60: 101–110).

Anti-atherosclerotic Effects

The cultured cells derived from atherosclerotic plaques of human aorta were used. On the seventh day in primary culture, the compound of the invention (final concentrations, $10^{-9}$ M, $10^{-8}$ M, $10^{-7}$ M, $10^{-6}$ M, $M^{-5}$ M and $10^{-4}$ M) was added to cell cultures in quadruplicate, control cells were cultured in standard medium. After 24 hours incubation, intracellular total cholesterol content was determined. Intracellular lipids were extracted with hexane-isopropanol mixture (3:2 vol/vol) (Hara, A. and Radin, N. S., *Anal. Biochem.* 1978, 90: 420–426). The total cholesterol content of the lipid extracts was determined using Boehringer Mannheim Monotest, Cholesterol CHOD-PAP method (Boehringer Mannheim GmbH, Mannheim, Germany).

Total cholesterol content was determined in cell culture incubated without drug (eight wells). The values obtained served as the control ones. The results were expressed as per cent of control. For confirmation of anti-atherosclerotic activity, further independent experiments on cell culture obtained from two other cell isolations were performed. Thus, the final conclusion was based on the results of at least three independent experiments.

Anti-atherogenic Effects

The cultured cells derived from grossly normal intima of human aorta were used. On the seventh day in primary culture, the cells were supplemented with Media 199 containing 40% human atherogenic serum from coronary atherosclerotic patient, control cells were cultured in standard medium. The tested compounds (the above-mentioned final concentrations) were added to cell cultures in quadruplicate. After 24 hours incubation, intracellular total cholesterol content was determined.

For confirmation of anti-atherogenic activity, the same procedure was done as described above.

Results

Anti-atherosclerotic Effects

Anti-atherosclerotic effects, i.e. effects imitating the regression of atherosclerosis in a cell culture, were examined on smooth muscle cells derived from fatty streaks and atherosclerotic plaque, as described above. These cells differ considerably from the normal cells cultured from uninvolved intima in their cholesterol content. The mean cholesterol content in the cells cultured from the plaque was five-fold higher than in the cells cultured from uninvolved intima.

During a 24 hour incubation, the compound of the invention at $10^{-8}$ M to $10^{-5}$ M decreased significantly total cholesterol content of cells cultured from atherosclerotic lesions of human aorta. The effect was observed in all independent experiments. The lowering of cellular cholesterol content was between 20% and 24%.

Anti-atherogenic Effects

In order to reveal anti-atherogenic activity, i.e. the activity imitating the prevention of atherosclerosis at the cell level, smooth cells of uninvolved human aortic intima were used and atherogenic serum obtained from patients with coronary atherosclerosis, as described above. This serum induced a statistically significant 1.3- to 1.6-fold increase in the cholesterol content of cultured cells. Increment of the cholesterol content over the standard level was assumed as 100% atherogenic effect.

In all experiments the compound of the invention decreased cholesterol accumulation caused by atherogenic serum. This effect was always observed at concentrations $10^{-5}$ M and $10^{-6}$ M. These concentrations decreased the serum atherogenicity by 48% and 56% on an average, respectively.

We claim:

1. A method for treating a human suffering from or susceptible to atherosclerosis, which comprises administering an effective anti-atherosclerotic amount of a compound of the formula:

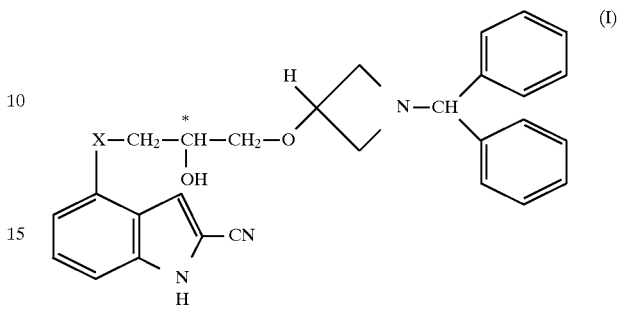

wherein X is —O— or —NH—, or a pharmaceutically-acceptable acid addition salt thereof.

2. The method according to claim 1 wherein X is —O—.

3. The method according to claim 2 wherein said compound is S-4-[3-(1-diphenylmethylazetidin-3-oxy)-2-hydroxypropoxy]-1H-indole-2-carbonitrile, or a pharmaceutically-acceptable acid addition salt thereof.

4. The method according to claim 1 wherein X is —NH—.

5. The method according to claim 4 wherein said compound is R-4-[3-(diphenylmethylazetidin-3-oxy)-2-hydroxypropylamino]-1H-indole-2-carbonitrile, or a pharmaceutically-acceptable acid addition salt thereof.

* * * * *